United States Patent
Rodrigues et al.

(10) Patent No.: US 8,604,079 B2
(45) Date of Patent: Dec. 10, 2013

(54) SOLID COSMETIC COMPOSITION

(75) Inventors: Adriana Amaral Rodrigues, Valinhos (BR); Claudia Léo, São Paulo (BR)

(73) Assignee: Nature Cosmeticos S.A., Sao Paulo (BR)

( * ) Notice: Subject to any disclaimer, the term of this patent is extended or adjusted under 35 U.S.C. 154(b) by 918 days.

(21) Appl. No.: 12/039,200

(22) Filed: Feb. 28, 2008

(65) Prior Publication Data

US 2009/0022679 A1 Jan. 22, 2009

Related U.S. Application Data

(63) Continuation of application No. 10/531,555, filed as application No. PCT/BR03/00147 on Oct. 15, 2003, now abandoned.

(30) Foreign Application Priority Data

Oct. 15, 2002 (BR) ..................................... 0207052

(51) Int. Cl.
*A61K 31/23* (2006.01)
*A61K 31/695* (2006.01)
*A61K 47/30* (2006.01)
*A61K 47/32* (2006.01)
*A61K 8/00* (2006.01)
*A61K 8/18* (2006.01)
*A61Q 1/02* (2006.01)
*A61Q 1/04* (2006.01)
*A61Q 1/06* (2006.01)

(52) U.S. Cl.
USPC ....... 514/552; 514/63; 514/772.3; 514/772.4; 424/63; 424/64

(58) Field of Classification Search
None
See application file for complete search history.

(56) References Cited

U.S. PATENT DOCUMENTS

| 5,053,079 | A | 10/1991 | Haxell et al. |
| 5,684,178 | A | 11/1997 | Philippe et al. |
| 6,258,346 | B1 | 7/2001 | Scavone et al. |
| 2004/0013624 | A1 | 1/2004 | Mateu et al. |
| 2004/0197286 | A1 | 10/2004 | Robert et al. |
| 2004/0258721 | A1 | 12/2004 | Bauer et al. |

FOREIGN PATENT DOCUMENTS

| EP | 1 147 761 | 10/2001 |
| GB | 2 167 662 | 6/1986 |
| WO | WO 00/69484 | 11/2000 |

OTHER PUBLICATIONS

International Search Report for PCT/BR03/00147 completed Jan. 30, 2004.
Bareco Product Data; Polywax Polyethylenes; Nov. 1981; XP002268647.
Anonymous; New Phase Technologies Performance Polymers; Internet; Online 1999; Retrieved from the Internet: <URL:http://www.suppliercd.com/scd10/NEWP0001/Attach/m0002402.pdf>; retrieved on Jan. 27, 2004; XP002268436.
Prof. Dr. Jürgen Falbe and Prof. Dr. Manfred Regitz; Römpp Chemie Lexikon; 1995; pp. 3886, 4130, 4131; vol. 5; Georg Thieme Verlag; Stuttgart; XP002266416 (3 sheets).

*Primary Examiner* — Sreeni Padmanabhan
*Assistant Examiner* — Jody Karol
(74) *Attorney, Agent, or Firm* — Alston & Bird LLP

(57) ABSTRACT

The present invention relates to a solid cosmetic composition comprising, as a structure agent, a combination consisting of a saturated straight-chain polymer and an agglutinating agent for this polymer.

The composition of the invention has a rigid, moldable and stable structure, being suitable for application as, for example, lipstick, blush, eye shadow, stick base, lip protectors (either colorful or colorless), deodorants, perfumes, among others.

5 Claims, 9 Drawing Sheets

SOLID COSMETIC COMPOSITION

CROSS-REFERENCE TO RELATED APPLICATIONS

This application is a continuation of U.S. application Ser. No. 10/531,555 filed Apr. 15, 2005 now abandoned, which was a national stage filing under 35 U.S.C. 371 of PCT/BR2003/000147 filed Oct. 15, 2003, which International Application was published by the International Bureau in English on Apr. 29, 2004, both of which are hereby incorporated herein in their entirety by reference.

FIELD OF THE INVENTION

The present invention relates to solid cosmetic compositions for application as, for example, lipstick, blush, eye shadow, stick base, lip protectors (either colorful or colorless), deodorants, perfumes, and others.

BACKGROUND OF THE INVENTION

There are many cosmetic compositions that are used for coloring and protecting lips, eyes, faces, etc.

As far as lipsticks are concerned, for example, those used at present are cosmetic compositions containing structural agents such as waxes, which are products traditionally used by the consumers. However, these products are heavy, because, when applied to the lips, they are noticed, since they form a film of translucent color, without a perfect and intense covering right at the first application.

Other types of lipsticks that use mixtures with linear structural agents exhibit a non-satisfactory spreadability, and one feels the friction of the lipstick while passing it on one's lips.

As it is known, lipsticks are a complex mixture of solids, semisolids and liquids, such as waxes and emollients that, as time passes, often exudes and undergo oxidation, rendering the appearance and odor of such a product unsatisfactory.

On the other hand, lipsticks with a high concentration of emollients have the problem of flowing through the lips' edges, in addition to having low fixation power.

Many of these problems related to a poor fixation of the product and its unpleasant feeling on the skin also occur with other forms of presentation of solid cosmetic compositions such as blushes, eye shadows, stick-bases, deodorants and the like.

Therefore, it is an objective of the present invention to provide a solid cosmetic composition that can be applied in the form of a bullet or a stick, which can provide the user with a feeling of not using any product.

SUMMARY OF THE INVENTION

The present invention relates to a solid cosmetic composition comprising, as a structure agent, a combination consisting of a saturated straight-chain polymer and an agglutinating agent for this polymer.

DETAILED DESCRIPTION OF THE INVENTION

Figure 1:
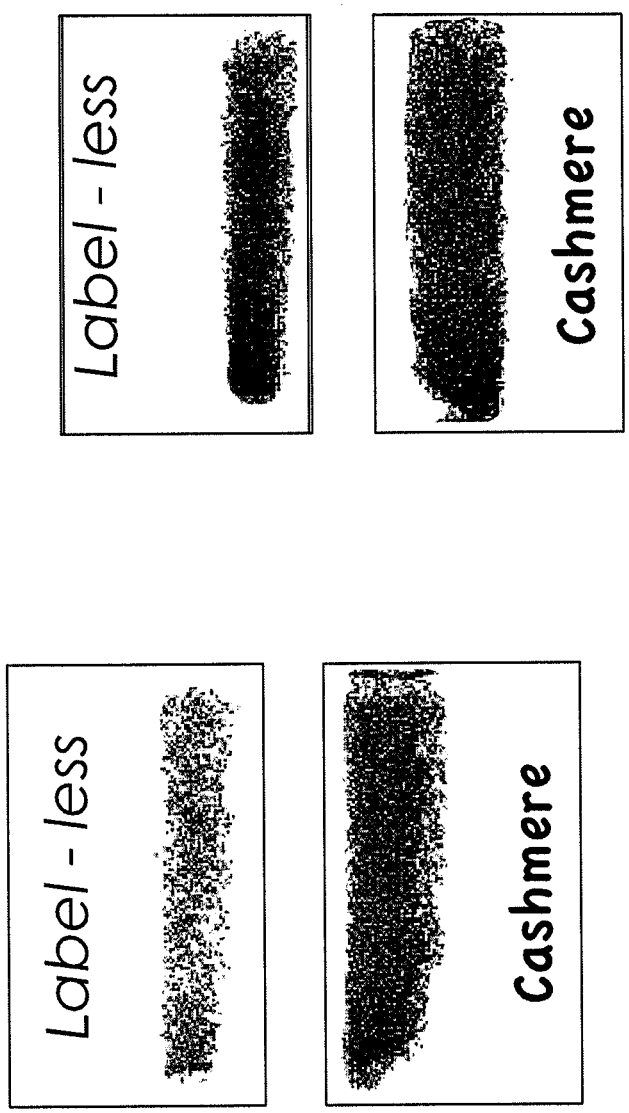
FIGS. 1 and 2 show images of the cosmetic composition of the invention compared with known compositions that are scanned from samples tested (in replicate) by sliding on a universal assay machine.

The present inventors have developed a novel cosmetic composition, the innovation of which lies in obtaining a rigid, moldable and stable structure, which is obtained by using a combination of two structural agents, namely a polymer with a specific structure and an agglutinant.

This rigid, moldable and stable structure is composed of a straight-chain aliphatic hydrocarbon with structural properties, and more specifically a polymer. This polymer is obtained by means of a polymerization process, controlled so as to ensure that its chain will be totally straight, without branches at the polymeric chain.

A polymer specially useful for the present invention is the totally saturated polyethylene with a molecular weight ranging from 300 to 700 and, more preferably, a saturated linear polyethylene with a molecular weight of approximately 400.

Together with the saturated linear polymer mentioned above, the solid cosmetic composition of the invention comprises an agglutinating agent for that polymer. In order for the resulting structure to have a stable form, it is necessary to use such an agglutinating agent, which, combined with said polymer, provides the desired moldability, as for example, the shape of a bullet in a stable stick. This agglutinating agent is a glyceride, formed by glyceryl esters and behenic acid, and preferably the triglyceride of behenic acid, known as Tribehenin.

It should be pointed out that some agglutinating agents used in cosmetic compositions and more particularly in lipsticks are mixtures containing glyceryl behenate and glyceryl dibehenate, which renders the composition unstable, polyethylene waxes, which provides the so-called lipstick bullet with a soft consistency, and esters such as triisostearoyl citrate, which provide an oily feeling on the lips.

Tribehenin may be used in cosmetic compositions as an occlusive skin conditioning agent, suspending agent, gel forming agent and as a brightener. When used in the present invention, its function is structural and as an agglutinating agent for a totally linear and saturated polymer.

Thus, a stable cosmetic composition with only two structural agents is obtained, without adding any type of mineral, vegetable and animal wax, more specifically natural waxes, or oils, which would make the product "heavier".

The saturated linear polymer is usually employed in a range of 2 to 20% by weight, based on the total weight of the composition. On the other hand, the agglutinant agent is advantageously employed in a proportion ranging from 3 to 15% by weight, also based on the total weight of the composition.

Since the structure of the composition is predominantly composed of a structural agent having a totally straight and saturated chain, this composition has an ultrafine texture and provides a feeling of absence of products on the lips, because it combines extremely light and comfortable structural agents that may be used with non-oily emollients, defining the so-called feeling of a "second skin".

In addition to the above-cited structural components, the composition of the invention contains other components that are usually employed in cosmetic compositions of this kind and that are determinative of the objectives of the invention. The composition may contain, for example, film forming agents, which provide greater fixation of the product and, in the case of lipsticks, help to prevent it from flowing into the upper and lower creases on the lips. For instance, the addition of dimethiconol fluoroalcohol dilinoleic acid, which is a film forming agent, promotes deaeration of the product in its manufacture, which is an additional technical advantage.

Compounds that inhibit oily characteristics of the composition may also be used, such as hydrogenated polyisobutene and isononyl isononanoate, in addition to compounds that provide treatment benefits such as maintenance of skin hydration and anti-free radical action. Examples of such compounds include spheres of marine biopolymers and vitamin E, respectively.

Specifically when formulated as a lipstick, the solid cosmetic composition of the invention may include compounds such as phenylethyl dimethicone, which promotes the achievement of luminosity on the lips, as well as ground dispersions in triisostearoyl citrate with the pigments having a reduced particle size, which provide a luminosity increase in the color of the product.

Chemical and physical sunscreens, in amounts sufficient to provide a sun protection factor (SPF) suitable for the final use, may also be added. In the case of lipstick, it is desirable for the sunscreens to be in an amount sufficient to provide a sun protection factor of at least 15.

In a preferred embodiment of the invention, the cosmetic composition comprises at least two film forming agents, more specifically trimethyl-siloxysilicate dissolved in cyclomethicone and dimethiconol fluoroalcohol dilinoleic acid, which guarantees long duration of the product, as well as enhances the fixation of the composition without flowing into neighboring areas, such as eyes, lips, etc. Since dimethiconol fluoroalcohol dilinoleic acid is a compound having the property of reducing the surface tension, it eliminates the step of deaerating the composition during the process or manufacturing and/or packing it.

As a demolding agent, a mixture of silicone oil and polyisobutene is used, more specifically polydimethylsiloxane and hydrogenated polyisobutene, which provide the appearance of the bullet with a satiny brightness, after the finishing process in packing the product, in order to provide the appearance which the consumer likes.

A composition prepared with the structural agents according to the present invention has a number of improved characteristics in comparison with analogous compositions of the prior art, namely:
- It has an ultrafine texture, which provides the feeling of absence of product after application thereof, be it on the lips, face, eyes, or elsewhere, leaving no oily or heavy feeling;
- It is a homogeneous film-forming composition, extremely light in weight and comfortable;
- It allows the product to slide in an intense way, without friction while it is being applied;
- It also provides color deposit in an intense way in the first application, when used in make-up products;
- It has a high refraction index, providing luminosity;
- It has long durability;
- It does not comprise toxic or irritating components.

Tables 1-4 illustrate examples of compositions formulated in accordance with the embodiments of the present invention, indicating their preferred components and appropriate quantitative ranges according to the final uses intended. All the concentrations indicated are defined as percentage by weight based on the total weight of the composition:

TABLE 1

Lipstick Composition

| Components | Function | Concentration (%) |
| --- | --- | --- |
| Phenylethyl dimethicone | Brightening agent | 8-15 |
| Cyclomethicone/ Trimethylsiloxysilicate | Film forming agent | 3-10 |
| Hydrogenated polyisobutene | Emollient | 10-20 |
| Propylparaben | Preservative | 0.01-0.10 |
| Hydroxy butyl toluene | Antioxidant | 0.01-0.10 |
| Tribehenin | Agglutinating agent | 3-15 |
| Polyethylene | Structure agent | 2-20 |
| Isononyl isonanoate | Vehicle | 10-30 |
| Dimethiconol fluoroalcohol dilinoleic acid | Film forming and deaerating agent | 1-5 |
| Titanium dioxide | Sunscreen | 0.1-2 |
| Octylmethoxycinamate | Sunscreen | 2-5 |
| Benzophenone 3 | Sunscreen | 1-3 |
| Active | Hydrating agent | 0.01-1 |
| Pigments (organic, inorganic, lacquers and mica) | Coloring agent | 15-25 |
| Triisostearoyl citrate | Emollient | 5-20 |
| Vitamin E | Anti-free radicals | 0.1-1 |
| Essence | Perfume | 0.1-1 |

TABLE 2

Pot Molded Bright Lipstick Composition

| Components | Function | Concentration (%) |
| --- | --- | --- |
| Diisostearyl malate | Emollient | 15-25 |
| Triisostearoyl citrate | Vehicle | 20-40 |
| PVP/eicosane copolymer | Film forming agent | 3-7 |
| Propylparaben | Preservative | 0.01-0.10 |
| Hydroxyl butyl toluene | Antioxidant | 0.01-0.10 |
| Tribehenin | Agglutinating agent | 3-15 |
| Polyethylene | Structure agent | 2-20 |
| Octylmethoxycinamate | Sunscreen | 2-5 |
| Benzophenone 3 | Sunscreen | 1-3 |
| Active | Hydrating agent | 0.01-1 |
| Pigments (organic, inorganic, lacquers and mica | Coloring agents | 1-15 |
| Vitamin E | Anti-free-radical | 0.1-1 |
| Essence | Perfume | 0.1-1 |

TABLE 3

Lip Protector Composition with Sun Protection Factor SPF 30

| Components | Function | Concentration (5) |
| --- | --- | --- |
| Dicapryl carbonate | Vehicle | 35-55 |
| Shea Butter | Emollient | 1-6 |
| PVP/eicosane copolymer | Film forming agent | 2-5 |
| Methylparaben | Preservative | 0.01-0.20 |
| Propylparaben | Preservative | 0.01-0.10 |
| Hydroxyl butyl toluene | Antioxidant | 0.01-0.10 |
| Tribehenin | Agglutinating agent | 3-15 |
| Polyethylene | Structure agent | 2-20 |
| Octylmethoxycinamate | Sunscreen | 5-10 |
| Benzophenone 3 | Sunscreen | 3-6 |
| Butyl methoxy dibenzoyl methane | Sunscreen | 2-5 |
| Octyl triazone | Sunscreen | 2-5 |
| Vitamin E | Anti-free-radical | 0.1-1 |
| Essence | Perfume | 0.1-1 |

TABLE 4

Stick-Base Composition
STICK-BASE FORMULATION

| Components | Function | Concentration (%) |
|---|---|---|
| Triglycerol-4 isostearate | Emollient | 0.1-2 |
| Dicapryl carbonate | Vehicle | 15-25 |
| Hydrogenated polyisobutene | Emollient | 5-15 |
| Stearyl dimethicone | Film forming agent | 2-8 |
| Silicone elastomer | Emollient | 2-10 |
| Nylon 12 | Sensorial modifier | 0.5-3 |
| Micronized talc | Absorber | 2-10 |
| Modified starch | Sensorial modifier | 5-15 |
| Silica microspheres | Absorber | 1-5 |
| Mixtures of preservatives | Preservative | 0.01-0.50 |
| Methylparaben | Preservative | 0.01-0.20 |
| Propylparaben | Preservative | 0.01-0.10 |
| Hydroxyl butyl toluene | Antioxidant | 0.01-0.10 |
| Tribehenin | Agglutinating agent | 3-15 |
| Polyethylene | Structure agent | 2-20 |
| Butyl methoxy dibenzoyl methane | Sunscreen | 2-5 |
| Titanium dioxide | Sunscreen | 10-15 |
| Active | Hydrating agent | 0.01-1 |
| Pigments (organic, inorganic, lacquers and mica) | Coloring agents | 2-12 |
| Vitamin E | Anti-free-radical | 0.1-1 |
| Essence | Perfume | 0.01-1 |

EXAMPLES

A lipstick composition as described above in Table 1 was subjected to a research, in which the product was tested by 120 volunteers for 7 days, with a use frequency of about 8.8 times. A few considerations are given below, where the values are averages on a concordance scale with 5 points at most:
- 4.8 points—it covers the lips in a homogeneous way;
- 4.6 points—it colors the lips at the first application;
- 4.7 points—it slides on the lips, transmitting a pleasant feeling of suavity;
- 4.4 points—the texture is light in weight like a plume;
- 4.4 points—it does not flow/it does not stain;
- 4.4 points—its color is not altered during use;
- 4.5 points—it has a differentiated, creamy and at the same time lighter emollience;
- 4.4 points—it protects one's lips;
- 4.4 points—it hydrates one's lips;

COMPARATIVE EXAMPLE

Eleven finished lipsticks were analyzed at the laboratories of the University of Campinas—UNICAMP and of the University of São Paulo—USP—São Paulo, Brazil, by Joekes, Nogueira and Cassiola, the samples being classified as follows:
- five packages containing compositions known from the prior art in the following color options: metallic wine color identified by the trade name ÉLUARD, metallic brown identified by the trade name DALI, red identified by the trade name PAINO golden identified by the trade name TECHNO, metallic rose color identified as "labelless";
- five packages containing compositions according to the present invention, as described in Table 1 in the following color options: metallic wine color identified by the trade name GEORGETTE, metallic brown identified by the trade name CETIM, red identified by the trade name MOUSSELINE, golden identified by the trade name ORGANZA, metallic rose color identified as Cashmere;
- a sample of the raw material saturated straight-chain polyethylene identified as "MP em bala" (MP in bullet).

In addition to the above-mentioned finished lipsticks, the following have been analyzed:
- a sample labeled "Bala do batom novo" (novel lipstick bullet), which is a base composition for the lipsticks according to the present invention;
- a sample labeled "Bala do batom velho" (old lipstick bullet), which is a base composition for the lipsticks of the prior art.

TABLE 5

Lipstick Composition of Traditional Formulation

| Components | Function | Concentration (%) |
|---|---|---|
| Castor oil | Vehicle | 10-50 |
| Carnauba wax | Structure agent | 1-5 |
| Candellilla wax | Structure agent | 5-10 |
| Bee wax | Structure agent | 1-6 |
| Ozoquerite wax | Structure agent | 0.1-1.5 |
| Ceresin | Structure agent | 1-5 |
| Hydrogenated castor oil | Emollient | 0.1-3 |
| Lanolin oil | Emollient | 2-7 |
| Decyl oleate | Emollient | 10-20 |
| Glyceryl abietate | Emollient | 0-3 |
| Hydrogenated vegetable oil | Thickener | 0.1-8 |
| Polybutene | Compacting agent | 0.1-15 |
| Isopropyl myristate | Emollient | 0.1-5 |
| Vitamin E | Anti-free-radical | 0.01-1 |
| Glyceryl rosinate/octyldodecyl myristate | Film forming agent | 0-5 |
| Propylparaben | Preservative | 0.01-0.10 |
| Hydroxyl butyl toluene | Anti-free-radical | 0.01-0.10 |
| Titanium dioxide | Sunscreen | 0-2 |
| Octylmethoxycinamate | Sunscreen | 0-5 |
| Benzophenone 3 | Sunscreen | 0-3 |
| Actives | Hydrating agent | 0-1 |
| Pigments (organic, inorganic, lacquers and mica) | Coloring agents | 1-30 |
| Essence | Perfume | 0.1-1 |

The test further used an A4-size sheet of trade mark Vitroskin:

1—DESCRIPTION OF THE TESTS AND RESULTS ACHIEVED

The finished lipsticks were separated in 5 pairs, each being composed of a lipstick of the invention and a lipstick of the prior art. Another pair was constituted by the samples labeled "Bala do batom novo" (invention=novel lipstick bullet) and "Bala do batom velho" (prior art=old lipstick bullet).

1.1—Sliding Tests:
Controlled Sliding

Two pairs of lipsticks and the pair of "bullets" were tested. Each pair was slide-tested only once, vertically and simultaneously, on pieces of Vitro-skin of dimensions 7.2 cm×1.5 cm at a speed of 0.5 cm s$^{-1}$ in a universal assay machine. Each piece of Vitro-skin was weighed before and after the sliding of the lipsticks. The sample masses deposited on these tests are indicated in Table 6 below.

TABLE 6

Sample masses deposited on the Vitro-skin substrate in the slide tests in a universal assay machine. Duplicates.

| Lipstick | Deposited mass, g | |
|---|---|---|
| Old lipstick bullet | 1.42 | 0.74 |
| Novel lipstick bullet | 2.38 | 1.92 |

TABLE 6-continued

Sample masses deposited on the Vitro-skin substrate in the slide tests in a universal assay machine. Duplicates.

| Lipstick | Deposited mass, g | |
|---|---|---|
| Label-less (*) | 1.27 | 1.70 |
| Cashmere (**) | 2.19 | 2.38 |
| Eluard (*) | 1.83 | 1.60 |
| Georgette(**) | 1.82 | 1.95 |

(*) lipstick according to the prior art
(**) lipstick according to the invention One can see, in this table, that the masses of sample deposited on the Vitro-skin are significantly larger in the case of the sample "Bala do batom novo" (novel lipstick bullet) than for the "Bala de batom velho" (old lipstick bullet). This difference is very well repeated for the lipsticks "Label-less" and "Cashmere", and in a greater degree for the lipsticks "Éluard" and "Georgette". Assuming that the lipsticks are obtained by formulation of the bases used in the "Balas" (bullets), one can perfectly discriminate the lipstick "Label-less" as coming from the base "Bala do batom novo" (novel lipstick bullet). The discrimination is not so good in the case of the lipsticks "Éluard" and "Georgette" and should be attributed to the differences in formulation.

Figure 2:
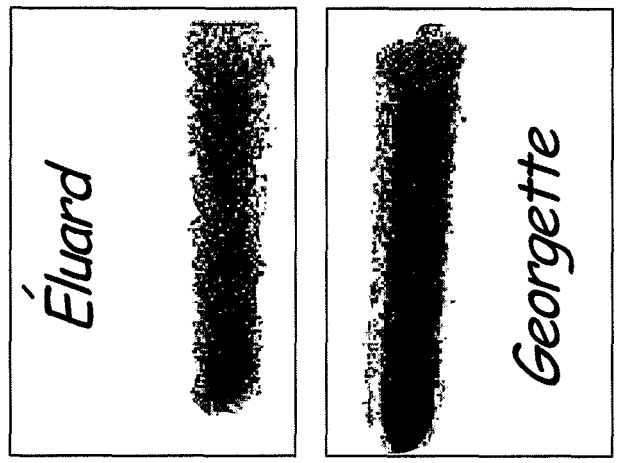
Figure 2:
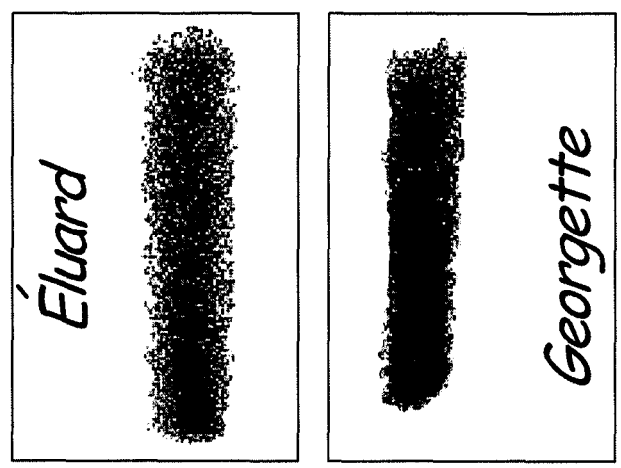

Pieces of Vitro-skin with lipstick were mounted in a scanner by using a glass spacer, in pairs. FIGS. 1 and 2 are the images obtained. These figures show well the differences in the amount of product deposited in each case, concordant with the gravimetry data.

Figure 3:
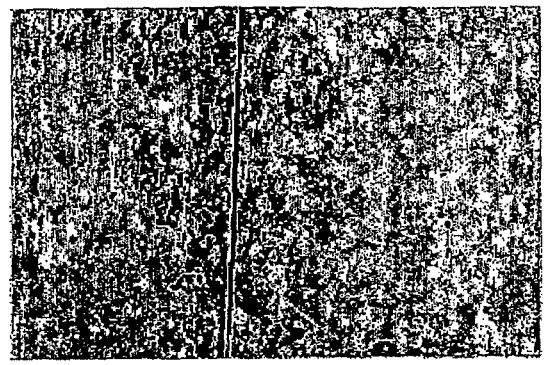
FIG. 3 shows images obtained by stereomicroscopy of the samples assayed by controlled sliding with an approximate 30-time enlargement.
Figure 3:
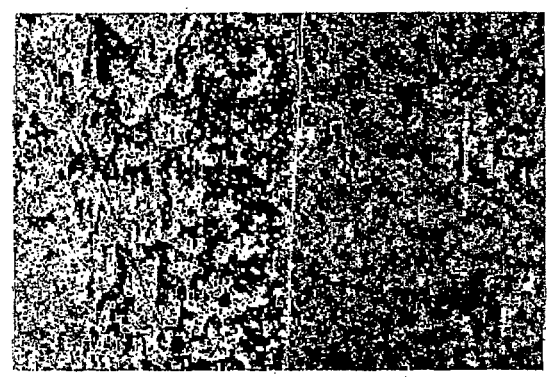
Figure 3:
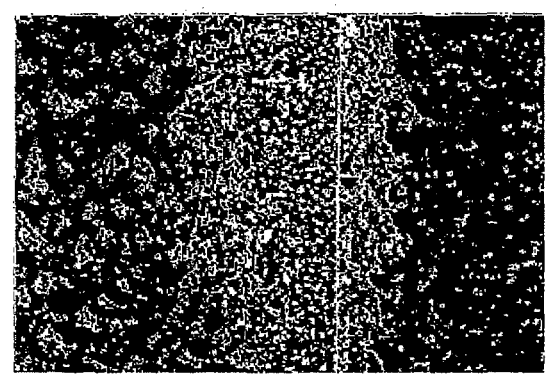

Other pieces of Vitro-skin were mounted between blade and tiny blade and photographed by stereomicroscope with dark field and illumination from below. FIG. 3 exhibits images obtained by stereomicroscopy of the samples tested by controlled sliding with an increase of about 30 times. The results are arranged in the following way:

at the top: "Bala do batom velho" (old lipstick bullet) on the left, and "Bala do batom novo" (novel lipstick bullet) on the right;
in the middle: "Label-less" on the left and "Cashmere" on the right;
below: "Éluard" on the left and "Georgette" on the right.

Just as in the scanner images, the differences in spreading are clear. With this greater increase one can note indicia of difference in the microstructure of the samples, which are confirmed in an analysis by SEM (scanning electronic microscopy).

1.2 Topography Analysis by Scanning Electronic Microscopy

The samples obtained in the controlled-slide tests were observed under an electronic microscope JEOL JSM 840 A, at the Laboratory of Electronic Microscopy of the Institute of Physics of the University of São Paulo—USP. A piece of dimensions 4 mm×7 mm was taken from each sample. These pieces were fixed with a double-face tape to the sample-holder and covered with gold by sputtering. The microscope was operated at 25 kV and current of $6\times10^{-11}$ A. The image recording was made on a white-and-black 135-mm photographic film, by using a photographic camera coupled to the SEM. FIGS. 5-9 are representative of the observations made with SEM.

Figure 4:
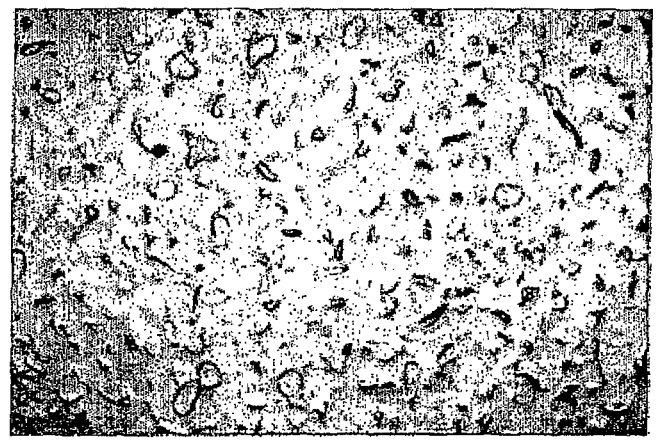
FIG. 4 shows an image obtained by transmission optical microscopy on Vitro-Skin™ of a sample analyzed with an approximate 100-time enlargement.
Figure 5:
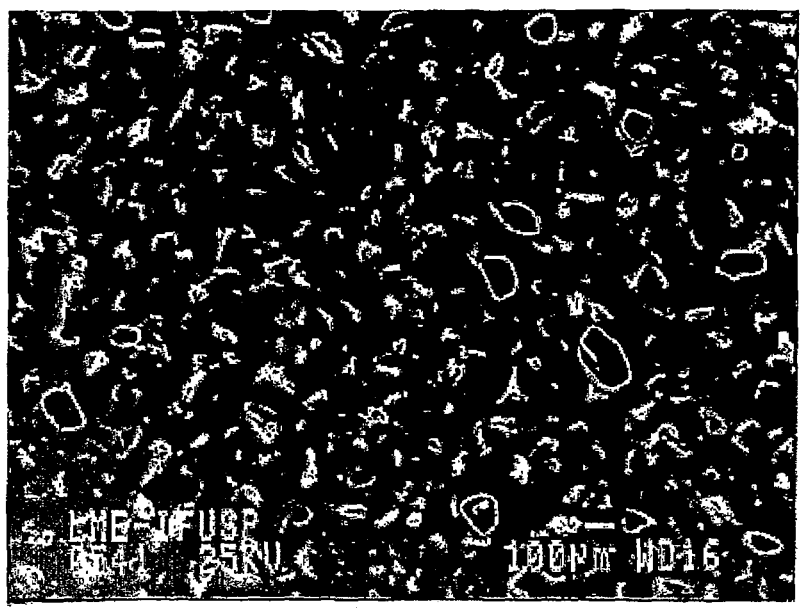
FIGS. 5 to 9 contain scanning electronic micrograph images of several analyzed samples.
Figure 5:
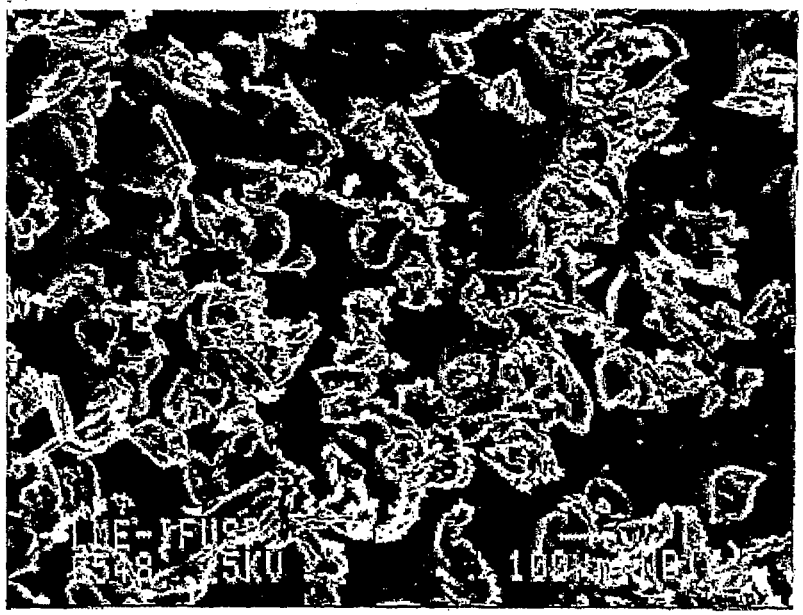

FIG. 4 shows the appearance of the Vitro-Skin™ under the optical microscope, incorporated herein only as an illustration. This is a quite homogeneous material in these enlargements, with roughness. FIG. 5A shows the topography of the Vitro-Skin™ (upper), in which the surface roughness is better characterized in comparison with the sample "MP em bala"—MP in bullet (lower).

FIG. 5B shows the aspect of the sample "MP em bala" (MP in bullet) manually spread on the Vitro-Skin™. It can be noted that the product spreads over the substrate, leaving particle aggregates in a quite irregular way.

Figure 6:
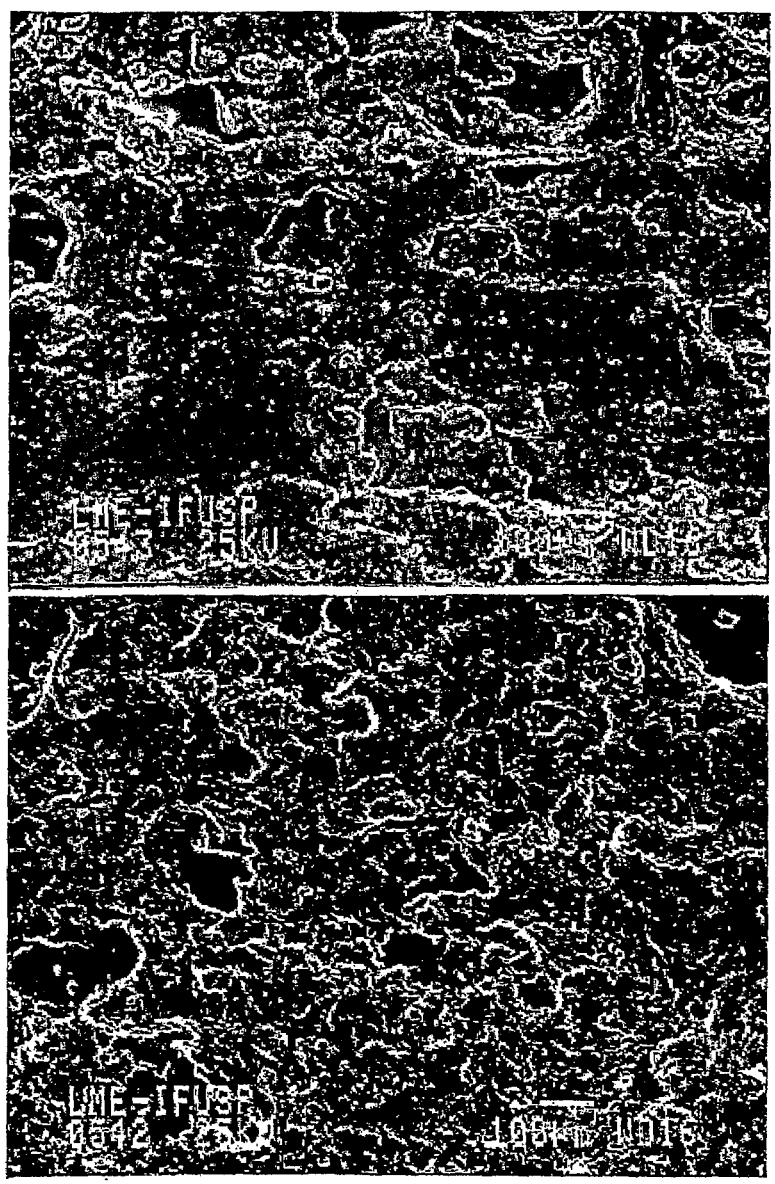

The micrographs A and B in FIG. 6 show the samples "Bala do batom velho" (old lipstick bullet) and "Bala do batom novo" (novel lipstick bullet), respectively, on the Vitro-Skin™. Both micrographs are strictly in the same enlargement. The spreading observed for the "Bala do batom velho" (old lipstick bullet) exhibits particle agglomerates of a greater size. The particles are rounded, providing a little-defined microstructure. The sliding between the different layers during the spreading seems to be not much uniform. The spreading observed for "Bala do batom novo" (novel lipstick bullet) shows greater uniformity. The particles are smaller, better defined and also form agglomerates of smaller size. These agglomerates present good cohesion with each other, providing greater uniformity of spreading. In bigger enlargements, not photographed, one can observe that the microstructure of the novel base has a higher level of structuring among the particles.

The observation of the spreading on the Vitro-Skin™ of the samples of the finished lipsticks has shown results similar to those presented in the micrographs A and B in FIG. 6. In FIG. 7A ("Label-less"), one notes lesser structuring of the sample and the formation of a thinner layer after the spreading than in FIG. 9B ("Cashmere"). In FIG. 7B, one again notes greater uniformity of the spreading.

Figure 7:
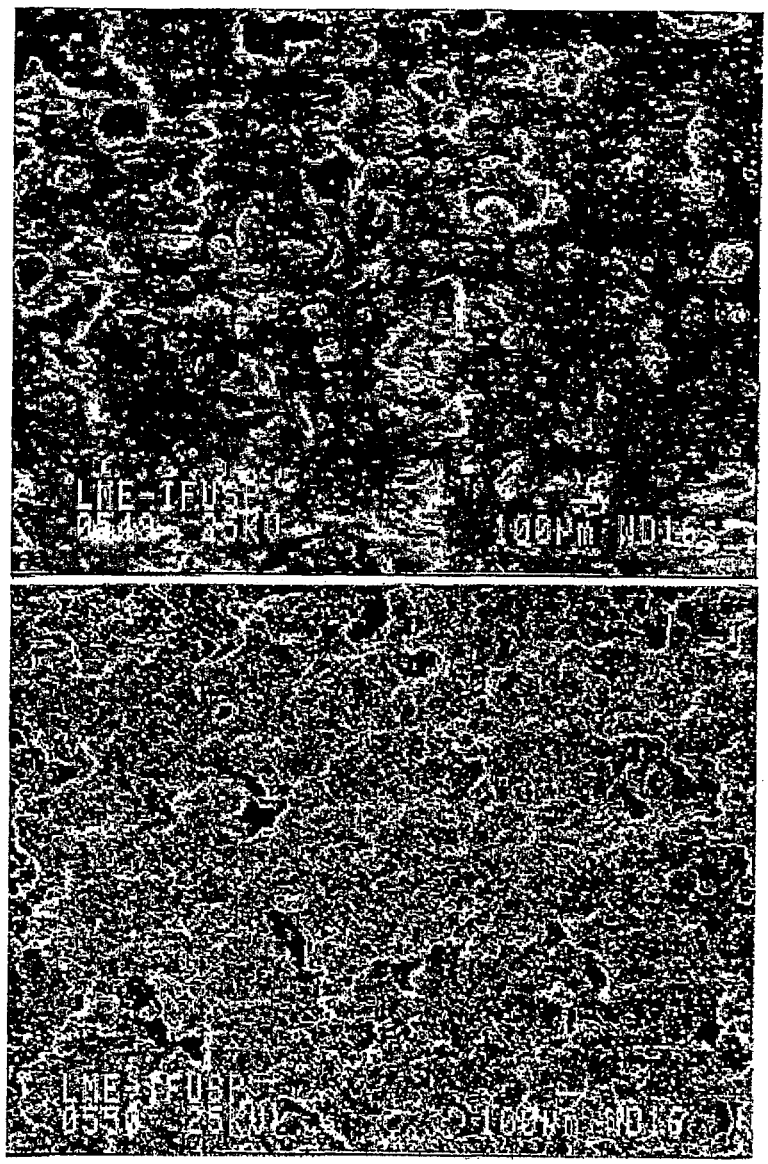
Figure 8:
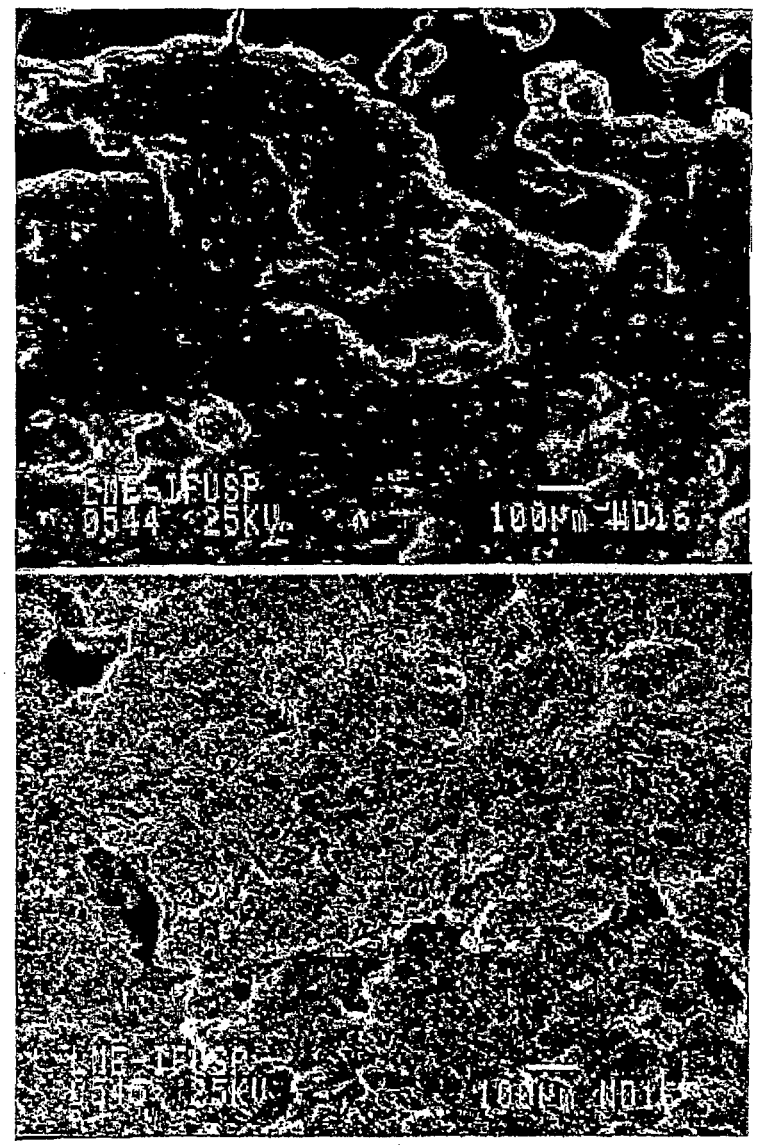

The micrographs of FIG. 8 exhibit an enlargement twice as big as that obtained for the micrographs of FIG. 7, the samples being the same. These micrographs confirm what was shown in FIG. 7. The sample of FIG. 8A has less structured microstructure and seems to spread in thinner layers (although the spreading has good cohesion among the particles) than in the sample of FIG. 8B.

Figure 9:
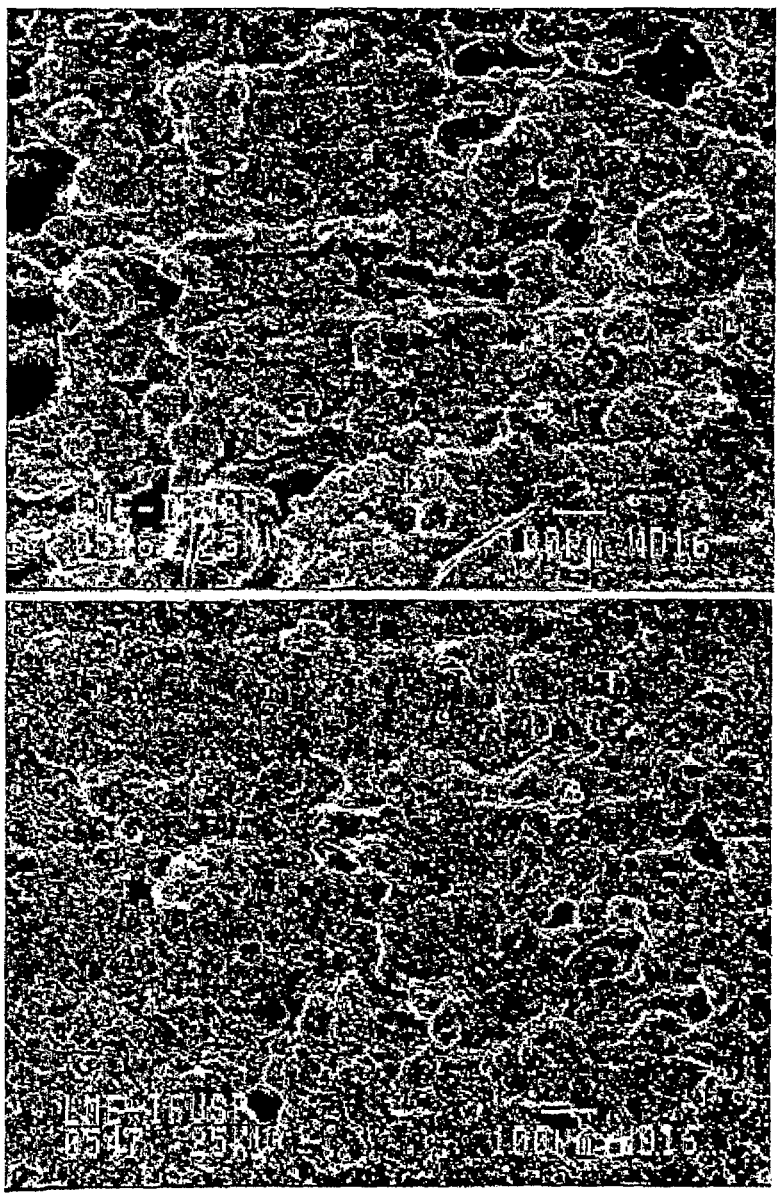

The pair of micrographs presented in FIG. 9 shows more clearly the differences observed before. FIG. 9A presents spreading on the Vitro-Skin™ of larger particle agglomerates, spreading in a less regular way and with less structuring. FIG. 9B shows smaller agglomerates, but evenly spread and particles having a more defined shape, more structured and with good cohesion among themselves.

2—CONCLUSIONS

The sliding tests show that there are significant differences between the lipsticks tested for the covering of the Vitro-Skin™ substrate. In all the cases, the finished lipsticks comprising compositions according to the invention cover the substrate more evenly.

The gravimetry tests show that these differences may be attributed to the nature of (said) based. The "Bala do batom novo" (novel lipstick bullet) deposits about twice as much product as the "Bala do batom velho" (old lipstick bullet) on the substrate in a single passing with controlled speed and force.

The tests with scanning electronic microscopy show that the microstructure of (said) bases is different, after spreading on the Vitro-Skin™. The "Bala do batom velho" (old lipstick bullet) spreads with formation of bitter agglomerates, with little structuring, but with good cohesion among the particles. The "Bala do batom novo" (novel lipstick bullet) spreads more densely and more evenly, with formation of smaller agglomerates, exhibiting a better structuring. The differences in structuring are also observed for the finished lipsticks. After having been spread, the finished lipsticks from the "Bala do batom novo" (novel lipstick bullet) exhibit a much more uniform microstructure than the lipsticks from the base "Bala de batom velho" (old lipstick bullet).

Thus, the larger and better spreading of the lipsticks according to the present invention with respect to the lipsticks of known composition of the prior art may be directly related to the different microstructure of the respective bases.

The invention claimed is:

1. A solid cosmetic composition characterized by comprising:
   a structure agent, the structure agent consisting of a combination of a linear polyethylene and tribehenin; and
   at least two film forming agents comprising trimethyl siloxysilicate dissolved in cyclomethicone and dimethiconol fluoroalcohol dilinoleic acid, and wherein the composition is characterized by the absence of mineral, vegetable, and animal waxes.

2. A composition according to claim 1, characterized in that the linear polyethylene has a molecular weight of approximately 400 Daltons.

3. A composition according to claim 1, characterized in that the linear polyethylene is present in a proportion ranging from 2 to 20% by weight, based on the total weight of the composition.

4. A composition according to claim 1, characterized in that the tribehenin is present in a range from 3 to 15% by weight, based on the total weight of the composition.

5. A composition according to claim 1, characterized in that it is in the form of a lipstick.

* * * * *

UNITED STATES PATENT AND TRADEMARK OFFICE
CERTIFICATE OF CORRECTION

| | | |
|---|---|---|
| PATENT NO. | : 8,604,079 B2 | Page 1 of 1 |
| APPLICATION NO. | : 12/039200 | |
| DATED | : December 10, 2013 | |
| INVENTOR(S) | : Rodrigues et al. | |

It is certified that error appears in the above-identified patent and that said Letters Patent is hereby corrected as shown below:

On the Title page,
Item (73) Assignee: "Nature Cosmeticos S.A." should read --Natura Cosmeticos S.A.--.

Signed and Sealed this
Eighth Day of April, 2014

Michelle K. Lee
*Deputy Director of the United States Patent and Trademark Office*